US007646845B2

(12) United States Patent
Lecomte et al.

(10) Patent No.: US 7,646,845 B2
(45) Date of Patent: Jan. 12, 2010

(54) METHOD AND SYSTEM FOR LOW RADIATION COMPUTED TOMOGRAPHY

(75) Inventors: Roger Lecomte, Sherbrooke (CA); Phillipe Berard, Laval (CA); Jules Cadorette, Ascot Corner (CA); David Lapointe, Pointe-Claire (CA)

(73) Assignee: SOCPRA Sciences Sante et Humaines S.E.C., Sherbrooke, Quebec (CA)

( * ) Notice: Subject to any disclaimer, the term of this patent is extended or adjusted under 35 U.S.C. 154(b) by 0 days.

(21) Appl. No.: 11/664,046

(22) PCT Filed: Sep. 28, 2005

(86) PCT No.: PCT/CA2005/001482

§ 371 (c)(1),
(2), (4) Date: Apr. 23, 2008

(87) PCT Pub. No.: WO2006/034585

PCT Pub. Date: Apr. 6, 2006

(65) Prior Publication Data

US 2008/0317200 A1    Dec. 25, 2008

Related U.S. Application Data

(60) Provisional application No. 60/613,219, filed on Sep. 28, 2004.

(51) Int. Cl.
*A61B 6/00* (2006.01)
(52) U.S. Cl. .......................................... 378/19; 378/4
(58) Field of Classification Search .................. 378/4, 378/19, 62; 382/132
See application file for complete search history.

(56) References Cited

U.S. PATENT DOCUMENTS 5,023,895 A * 6/1991 McCroskey et al. ............ 378/4
5,665,969 A   9/1997 Beusch .................. 250/370.09

(Continued)

OTHER PUBLICATIONS

Bert, et al., "Computed Tomography using the Medipixi1 Chip," *International Workshops on Radiation Imaging Detectors 4 (IWORID)*, (Sep. 11, 2002).

(Continued)

*Primary Examiner*—Irakli Kiknadze
(74) *Attorney, Agent, or Firm*—K&L Gates LLP

(57) ABSTRACT

A method for single photon counting transmission computed tomography (CT) is described. The method is based on an apparatus consisting of a radiation source and detectors on an opposite side of the subject from the source. The radiation source is for example an X-ray tube. The detectors are independently connected to parallel, fast, low-noise processing electronics capable of recording and counting individual X-ray photons at very high rate. In one embodiment of the invention, said detector is made of a scintillator coupled to a photodetector. The photodetector can be an avalanche photodiode (APD). The method comprises the steps of: directing the low energy radiation source toward the subject; detecting the radiation transmitted through the subject towards the detectors and recording the position and energy of each individual X-ray photon; rotating the radiation source and detectors around the subject; recording data for each position of the radiation source and detectors around the subject to form projections; and creating a CT image from the recorded projection data. The proposed method allows enhancing CT image contrast and reducing radiation dose to the patient by counting individual X-ray photons.

53 Claims, 4 Drawing Sheets

U.S. PATENT DOCUMENTS

| | | | |
|---|---|---|---|
| 2003/0043957 A1* | 3/2003 | Pelc | 378/4 |
| 2004/0096031 A1 | 5/2004 | Caria et al. | 378/62 |
| 2007/0140410 A1* | 6/2007 | Van Stevendaal et al. | 378/7 |

OTHER PUBLICATIONS

Johns et al., "Photon-Counting Detectors for Digital Radiography and X-Ray Computed Tomography," *Opto-Canada, SPIE Regional Meeting on Optoelectronics, Photonics, and Imaging SPIE TD01*, pp. 367-369, (May 2002).

Fischer et al., "A Counting CdTe Pixel Detector for Hard X-Ray and T-Ray Imaging," IEEE Transactions on Nuclear Science, Vo. 48, No. 6, pp. 2401-2404 (Dec. 2001).

Beuville, E., et al., "High Resolution X-ray Imaging Using a Silicon Strip Detector," *IEEE Transactions on Nuclear Science*, 45(6): 3059-3063, (Dec. 1998).

Cahn, R.N., et al., "Detective Quantum Efficiency Dependence On X-ray Energy Weighting In Mammography," *Med. Phys.*, 26(12): 2680-2683, (Dec. 1999).

Fontaine, R., et al., "Architecture of a Dual-Modality, High Resolution, Fully Digital Positron Emission Tomography/Computed Tomography (PET/CT) Scanner For Small Animal Imaging," *IEEE Transactions on Nuclear Science*, 52(3): 691-696 (Jun. 2005).

Paulus, M.J., et al., "A New X-ray Computed Tomography System for Laboratory Mouse Imaging," *IEEE Transactions on Nuclear Science*, 46(3): 558-564 (Jun. 1999).

\* cited by examiner

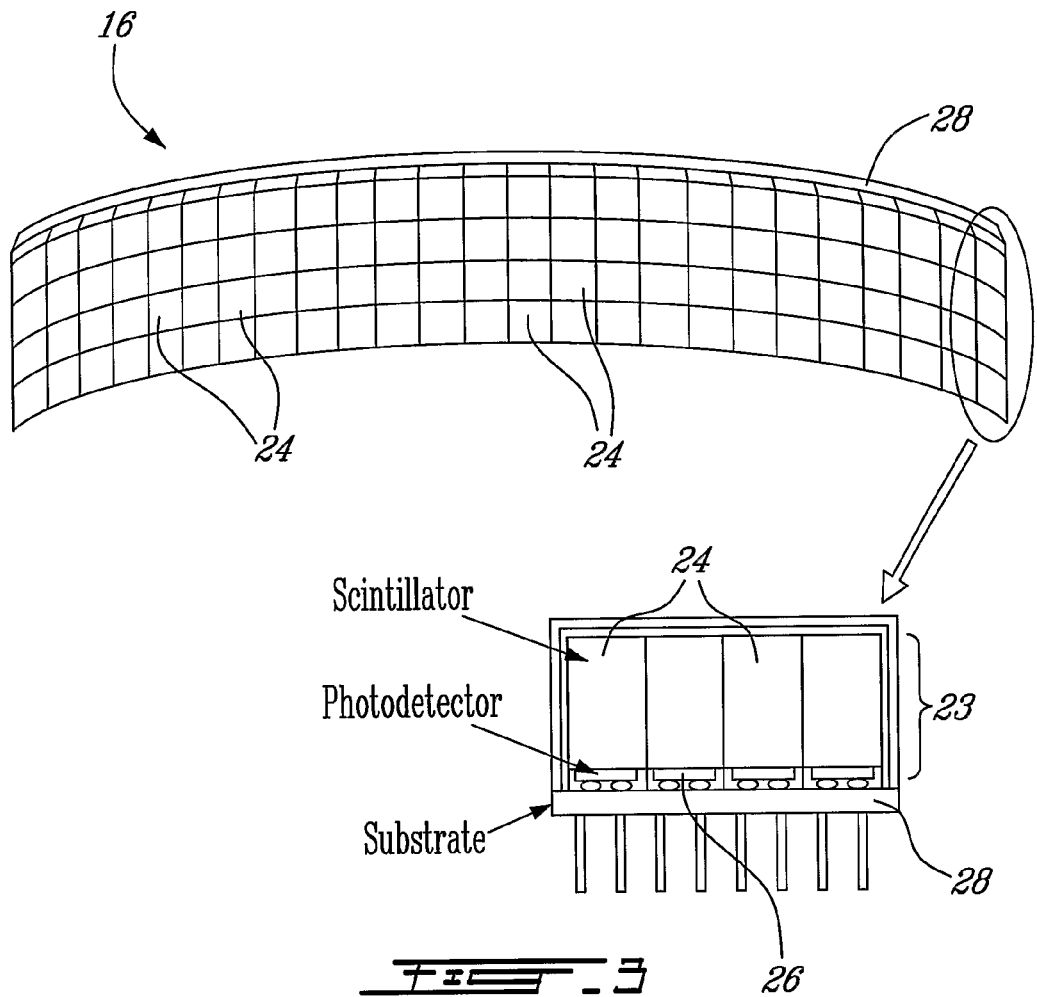
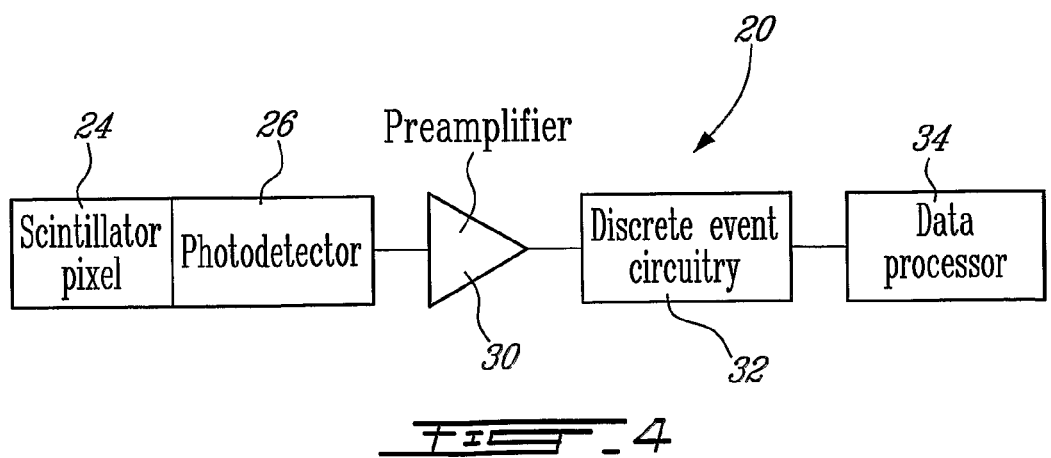

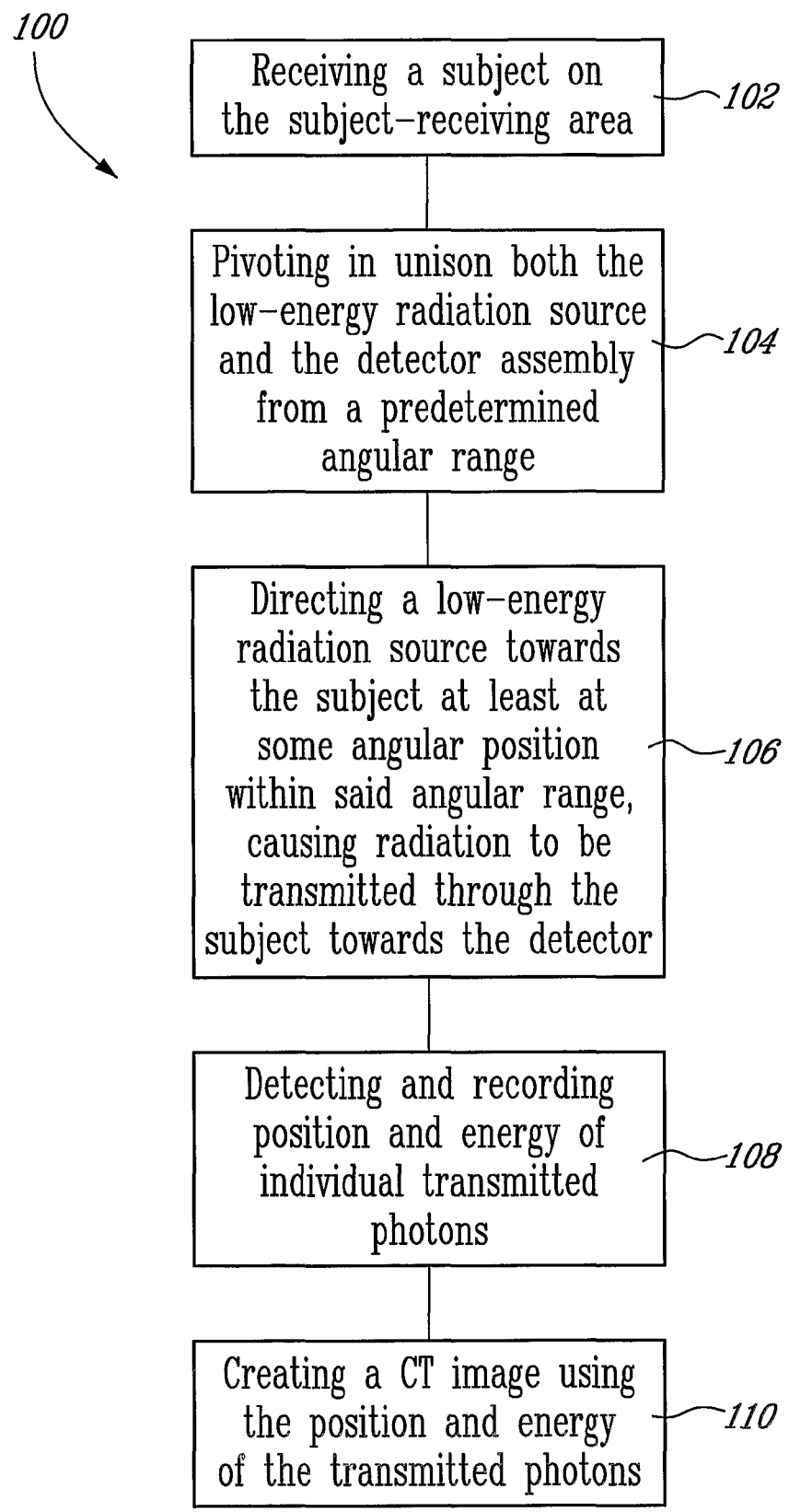

METHOD AND SYSTEM FOR LOW RADIATION COMPUTED TOMOGRAPHY

CROSS-REFERENCE TO RELATED APPLICATIONS

This application is the national phase of International (PCT) Patent Application Serial No. PCT/CA2005/001482, filed Sep. 28, 2005, published under PCT Article 21(2) in English, which claims priority to and the benefit of U.S. Provisional Patent Application Ser. No. 60/613,219, filed Sep. 28, 2004, the disclosures of which are incorporated herein by reference.

FIELD OF THE INVENTION

The present invention relates to transmission computed tomography (CT). More specifically, the present invention is concerned with a method and system for low radiation computed tomography.

BACKGROUND OF THE INVENTION

Computed tomography (CT) is a well-known method for obtaining images of the internal structure of a subject from its projections. In X-ray CT, these projections are obtained by rotating an external radiation source, usually an X-ray tube, around the subject and measuring the X-ray transmission through the field of view with an opposite X-ray detector array. The measured intensity of the transmitted X-ray flux through the subject, in reference to the measured intensity without the subject, provides a measure of the mean attenuation through the body tissues, which in turn provides information on the tissue density and composition. A set of projections, obtained over 180° or 360°, is then processed by a tomographic reconstruction algorithm which creates the cross sectional image.

CT has been shown to be superior to conventional radiography in the detection of a wide variety of diseases because of the greater contrast it allows to achieve. However, CT involves a considerably greater amount of radiation than conventional radiography or other tomographic imaging modalities such as Single Photon Emission Computed Tomography (SPECT) and Positron Emission Tomography (PET).

Modern CT scanners are used more and more for routine clinical check-up and they currently account for 30% to 50% of the radiation dose to the general population. In typical clinical CT diagnostic investigations, the radiation dose received by the patient typically exceeds the annual dose limit allowed to the normal population. This issue is particularly preoccupying in pediatric scanning, as the human body is still growing and more prone to developing cancer 10 or 20 years later as a result of dose exposure.

For repeated studies in the same subject, as it is required for example for preventive screening or patient follow-up, it is of utmost importance to reduce the radiation exposure to the minimum level compatible with the diagnostic application. However, reducing the radiation dose on CT procedures has the effect to increase image noise, thus reducing contrast, making lesions more difficult to detect and ultimately affecting diagnostic accuracy.

In micro-CT imaging of animal subjects, the typical radiation dose received in one single scan can represent as much as 10% of the LD50/30 for mice (the dose required to kill 50% of mice by 30 days after radiation exposure without other intervention). Significant short-term stimulation effects (DNA repair mechanisms, immune response, free-radical detoxification and apoptosis) and long-term effects of radiation-induced damage have been reported in this dose range, which may potentially have confounding biological effects biasing research results.

Current CT scanners employ ionization gas detectors (e.g., xenon), semiconductor diodes (Si, CdTe, CZT . . . ), phosphors coupled to charge-coupled devices (CCDs), or scintillators coupled to silicon diodes or photomultiplier tubes. Due to limitations in signal-to-noise ratio and/or count rate, these detectors must be operated in current mode, whereby the product of the mean X-ray event rate and the average X-ray energy is the measured parameter. Also depending on the material used for X-ray detection, the detector's quantum efficiency is sometime well below the ideal 100% value. As a consequence, no energy dependent processing (such as multi-spectral image analysis or scatter correction) may be performed. In spite of the fact that current mode CT involves a poor utilization of the information conveyed by the number and energy of the individual transmitted X-rays, it is well suited for high rate studies where high X-ray fluxes and fast scanning times are employed.

In another respect, the inherent integration of the X-ray beam energy has the detrimental consequence of exacerbating the so-called beam hardening effect, by increasing the weight of high energy X-rays relative to low energy X-rays proportionally to the X-ray photon energy. However, transmitted low energy photons convey more contrast information about soft tissue than transmitted photons at high energy. The ideal weight factor to achieve maximum contrast using spectral X-ray sources is proportional to $E^{-3}$ (where E is the incident photon energy) to reflect the attenuation properties of materials which follows the following equation in the diagnostic energy range [1]:

$$\mu(E) \approx \frac{N_0 \rho}{A}(aZ^{4.2}E^{-3} + bZ)$$

where $N_0$ is Avogadro's number, $\rho$ is the density, A is the atomic mass and Z is the atomic number. For integrating systems, which inherently take weight factor to be proportional to the photon energy, there is a difference of the order of $E^4$ relative to optimum weighting.

Another adverse consequence of X-ray integrating systems, which imposes strict stability requirements on the entire systems, is that the noise from all sources (electronic, variance due to scintillation photon or charge carrier statistics, afterglow in phosphors, systematic signal bias) is integrated and measured together with the signal in acquiring CT data, leading to noisier projection data and degraded image contrast. As a consequence, higher doses are required to overcome the intrinsic noise in the signal and to achieve the required contrast in the CT images. Another related consequence is that more powerful, cumbersome and expensive X-ray tubes with complex cooling systems must be used to reduce imaging times.

Single photon counting systems have been developed in some other imaging applications than CT, such as conventional scintigraphy, SPECT and PET. However, the signals from the detectors in most of these imaging systems are multiplexed or combined together in order to process the signals from a large number of detector elements (or pixels) using a smaller number of electronic channels. On one hand, the signal amplitude generated by the detectors in these applications (incident radiation>100 keV) is generally sufficient to allow sufficiently accurate computation of the position of interaction. On the other hand, this approach is advantageous to reduce the cost and complexity of the systems, but it greatly limits the maximum count rate per detector element that can be achieved, which is well below the mean count rate per unit area required in CT imaging.

Strip detector configuration made of semiconductor materials has been proposed to measure low energy radiation in the diagnostic X-ray range [2]. Such detectors, made of CdTe, CZT and Si, can operate at room temperature and provide adequate signal to noise ratio to measure the energy of individual X-ray photons with high accuracy. However, the multiplexing of $N^2$ detector pixels into 2N electronic channels reduces the maximum count rate per pixel by a factor of at least N/2 (neglecting the time required for decoding). It has been found that such a system is severely statistics limited for high-rate photon counting CT. The use of an individual readout channel per detector pixel was also found to be count rate limited due to the long charge collection time which increases dead time and severely limits the maximum event rate that can be processed [3]. Semiconductor detectors also suffer from low detection efficiency in the higher diagnostic energy range. Even though thicker semiconductor diodes has been proposed to overcome this problem, their use increases the cost of the detector and the charge migration time adds extra dead time that further limits the detector count rate.

Pixelated detectors made of high purity germanium (HPGe) have the advantage with respect to energy resolution of being capable of resolving the fine structure of X-ray spectra. However, such systems require detector cooling, typically to 77° K, and they must be used in conjunction with low-noise charge preamplifiers having a long integration time to collect the slow drifting charge carriers from the bulk of the detector material. Either in strip detector configuration or with an individual readout channel per detector pixel, pulse pile-up of the slow decaying signals from the charge preamplifiers limits the maximum count rate that can be reached with such detectors. Moreover, such systems are generally much too expensive to be considered for a large-scale application, such as medical imaging scanners.

Yet another method from the prior art for counting and measuring energy of individual X-ray photons is to read out detector pixels at a rate such that the likelihood of registering more than one X-ray photon per detector pixel during a readout period is negligible. The readout circuit is made of register cells and a controller to transfer the response in pixels to register readout cells. If the response of the detector pixels may be weighted according to the energy of the detected X-ray photon, a detection mechanism can be implemented for converting the response of the detector pixel into an electric signal (charge or current) that is proportional to the energy of the detected X-ray photon, assuming that the likelihood of arrival of more than one photon in the detector pixel during one readout period is negligible. A drawback of this method is that it requires ultra-low noise detectors and extremely fast readout rates to achieve the detector count rate required for use in CT imaging.

SUMMARY OF THE INVENTION

A method for single photon counting computed tomography (CT) is described. The method is based on an apparatus comprising a radiation source and detectors on an opposite side of the subject from the source. The radiation source can be an X-ray tube. The detectors are connected to parallel, fast, low-noise processing electronics capable of recording and counting individual X-ray photons at very high rate and measuring the energy of said individual X-ray photons.

The present invention comprises the steps of: directing the low energy radiation source toward the subject; detecting the radiation transmitted through the subject towards the detectors and recording the position and energy of each individual X-ray photon; rotating the radiation source and detectors around the subject to form projections; and creating a CT image from the recorded projection data.

More specifically, in accordance with a first aspect of the present invention, there is provided a method for computed tomography (CT) comprising:

providing a low energy radiation source oriented towards a subject-receiving area;

providing a detector assembly positioned beyond the low-energy radiation source relative to the subject-receiving area; the low energy radiation source and the detector assembly being pivotable in unison about the subject-receiving area;

receiving a subject on the subject-receiving area;

pivoting in unison both the low-energy radiation source and the detector assembly from a predetermined angular range;

directing the low-energy radiation source towards the subject at least at some angular position within the angular range, causing radiation to be transmitted through the subject towards the detector; the radiation transmitted through the subject towards the detector including transmitted photons;

detecting and recording position and energy of individual transmitted photons; and creating a CT image from the position and energy of the transmitted photons.

The CT images are acquired in "pulse mode" where each X-ray is individually detected and its position and energy are individually recorded in the corresponding projections. Current technologies for obtaining CT images operate in a current mode, where the average charge generated by the interactions of X-rays in a detector is being measured as a function of time during X-ray irradiation. Therefore, unlike traditional CT data acquisition, which cannot record the number and energy of the individual X-rays, the present system can perform multispectral analysis of the X-ray data set, providing an opportunity for beam hardening correction and more efficient separation of soft tissue image data from skeletal tissue data.

According to a second aspect of the present invention, there is provided a system for computed tomography (CT) comprising:

a subject-receiving area for receiving a subject;

a low energy radiation source oriented towards the subject-receiving area;

a photon-counting detector assembly positioned beyond the low-energy radiation source relative to the subject-receiving area; the low energy radiation source and the photon-counting detector assembly being pivotable in unison about the subject-receiving area; the photon-counting detector assembly including at least one detector pixel for detecting and recording position and energy of individual photons from the low energy radiation source transmitted from the subject;

photon-counting electronics coupled to each the photon-counting detector pixel for measuring and recording count-rate of the at least one detector pixel; and a signal processor coupled to the photon-counting electronics for creating CT image from the count-rate of the at least one detector pixel.

In single photon counting systems, all photons are given the same weight, which is an improvement compared to charge integration. Further improvement can be accomplished by approximating the weight of individual detected events proportionally to $E^{-3}$, which is close to the variation of attenuation cross section for photons in the radiologic energy range (10-100 keV). The inclusion of energy (or spectral) data in the image provides an additional means of improving soft tissue differentiation by reducing the effects of beam hardening and permits some degree of correction for scattered X-rays in the image. Moreover, the system allows providing higher contrast images for the same dose, or similar contrast images for a lower dose to the subject compare to CT system according to the prior art.

Other objects, advantages and features of the present invention will become more apparent upon reading the following non restrictive description of preferred embodiments thereof, given by way of example only with reference to the accompanying drawings.

BRIEF DESCRIPTION OF THE DRAWINGS

In the appended drawings:

FIG. 3 is a schematic view of the detector assembly from FIG. 2;

FIG. 4 is a block diagram of the photon-counting electronics from FIG. 2;

FIG. 7 is a flowchart of a method for low radiation computed tomography according to an illustrative embodiment of the present invention.

DETAILED DESCRIPTION

Figure 1:
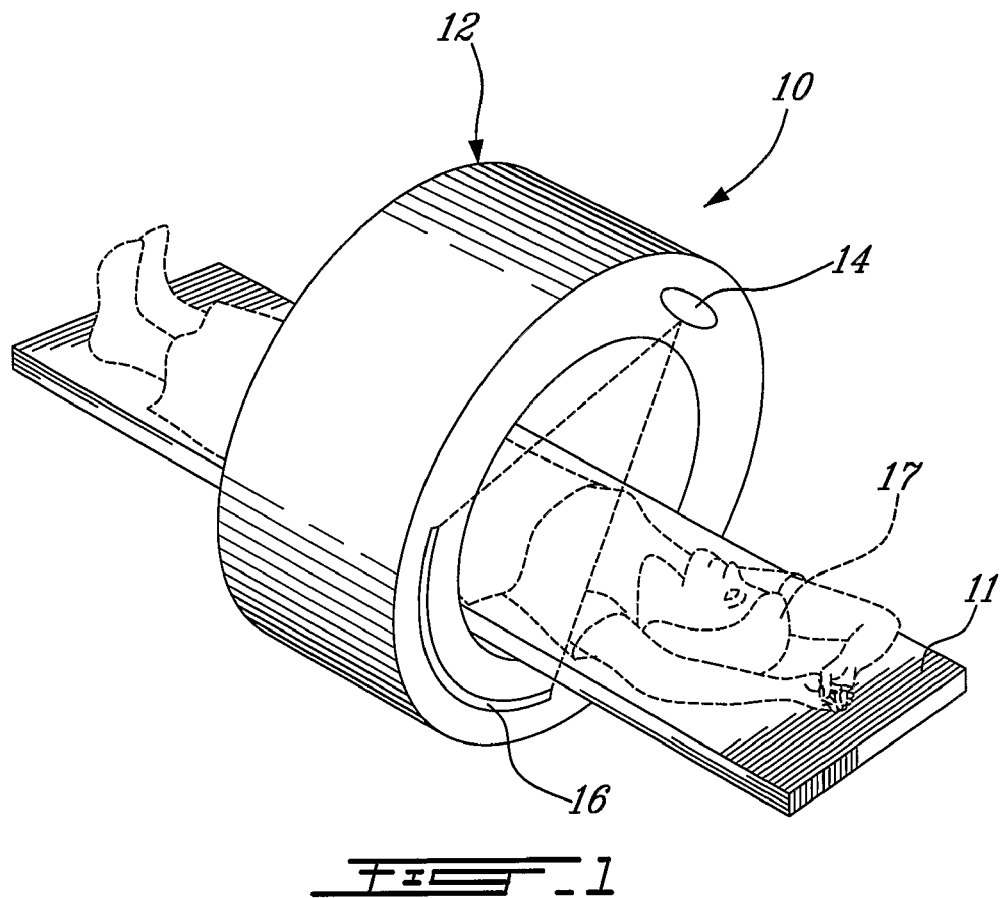
FIG. 1 is schematic perspective view of a system for low radiation computed tomography according to an illustrative embodiment of the present invention.

A system 10 for low radiation computed tomography according to an illustrative embodiment of the present invention will now be described with reference to FIGS. 1-2.

The system 10 comprises a subject-receiving area in the form of a bed 11 and an enclosure 12 partially surrounding the bed 11 containing a low energy radiation source, in the form of an X-ray source 14, and a detector assembly 16.

The enclosure 12 is generally in the form of a cylinder positioned about the bed 11 defining a tunnel therein. The X-ray source 14, is for example an X-ray tube mounted in the enclosure 12 so as to project a low energy radiation beam towards the radiation detector array 16 after passage through the patient 17.

The X-ray tube 14 may be for example of the microfocus or microfocus rod X-ray tube type.

Other types of X-ray sources including without limitations rotating targets and dual spots can also be used.

The detector assembly 16 is located in the enclosure opposite the radiation source 14 and therefore beyond the low-energy radiation source 14 relative to the bed 11.

Of course, the bed is suitable to receive a human 17 as illustrated in FIG. 1 or an animal (not shown).

The enclosure 12 is pivotally mounted about the table 11 in a well-known third generation CT scanner fashion. The bed 11 is movable along the enclosure pivoting axis. The system 10 can therefore be operated as an ultra-fast spiral CT scanner, suitable for three-dimensional (3D) volume imaging. Of course, the system 10 can be used to implement other generation CT scanner as will become more apparent upon reading the following description.

Of course, the bed and enclosure mounted to frame elements and made movable through conventional motors. Since such elements are well known in the art and beyond the scope of the present invention, they will not be described further in.

Figure 2:
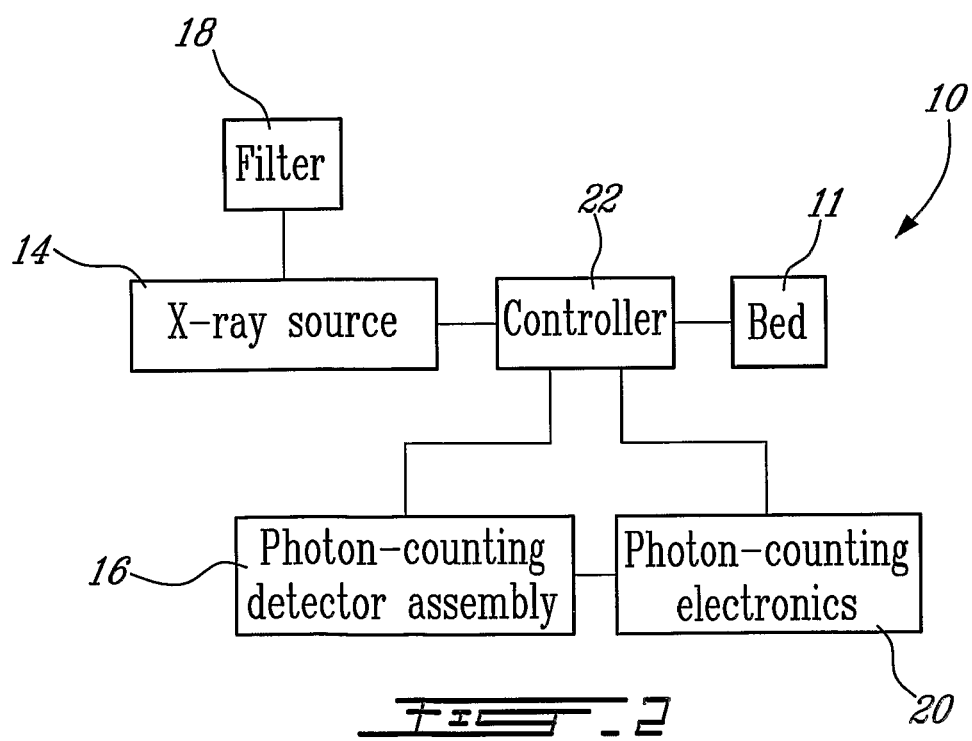
FIG. 2 is a block diagram of the system form FIG. 1.

Referring now more specifically to FIG. 2, the system 10 further comprises a filter 18 mounted to the enclosure 12 near the energy source 14 between the bed 11 and the source 14 so as to be operatively coupled thereto, photon-counting electronics 20 and a controller 22.

The X-ray beam is filtered to get certain mean beam energy to achieve maximum contrast sensitivity and lower dose for the subject size being scanned 17. The X-ray beam is also collimated so that only the useful field of view defined by the photon emission location and the detector array 16 is imaged.

The X-ray detector assembly 16 includes a plurality of detector pixels 23, comprised of a scintillator 24 with a corresponding photodetector 26 wherein each detector pixel 23 is capable of detecting X-ray photons received from an attenuated X-ray beam and processing detected events using fast photon counting electronics 20. The X-ray tube current is set to allow the discrimination and counting of each individual X-ray photons impinging on the detector pixels 23. A threshold is set above the electronic noise or above some energy level to allow noise and scattered photon rejection.

The X-ray tube parameters and detector array are controlled by a controller 22, which can be in the form of a computer, which also controls the motion of the bed 11 and the photon-counting detector assembly and electronics 16 and 20 acquisition parameters. The signals or number of counts registered by the detectors for each position of the X-ray source and detector arrays are then processed to form a complete projection data set or sinogram which can be used to reconstruct the cross-sectional image of a slice using reconstruction algorithms which are well known in the art. Finally, the reconstructed image can be supplied in a standard readable image format for viewing and analysis.

The detector assembly or detector array 16 will now be described in more detail with reference to FIG. 3.

The detector assembly 16 comprises an array of scintillators 24 defining scintillator pixels, each mounted on top of a respective photodetector 26 so as to be optically coupled thereto, each pair of scintillator pixel with a corresponding photodetector defining a detector pixel 23.

To maximize the count rate of the individual pixel 23, each scintillator 24 is optically isolated with reflector material and an optical coupling can be used on the interface between the scintillator 24 and the photodetector detective surface to improve the collection efficiency of scintillation light generated by the interaction of X-ray photons in the said scintillator. In contrast to conventional CT detectors, care is exercised to avoid light or charge sharing to occur between the different detection cells to avoid crosstalk or multiple event generation due to scintillation light or charge leaking to adjacent pixels. Similarly, scintillation materials having a high photoelectric interaction probability for X-ray in the diagnostic energy range are preferred to avoid multiple Compton interactions in adjacent pixels 23. The latter allows minimizing the rate of multiple events in adjacent pixels 23, which can either be recorded at the expense of a slight degradation of spatial resolution, or be rejected at the expense of increased dead time and reduced count rate.

Of course, in some embodiments, for example in cases where a plurality of crystal scintillators are mounted on a single photodetector, optical isolation may not be necessary on the interface between the scintillator 24.

The scintillators 24 are fast light emitting crystal enabling quick conversion of radiation into light photons and further into electric charge in the photodetector that can be read out and processed by the front-end electronics 20.

The scintillators 24 are for example made of a high density, fast and high efficiency light emitting crystal material such as cerium activated orthosilicate crystals. Examples of such crystal materials include LSO, LGSO and LYSO.

The scintillators can also be of the organic type, such as scintillators made of pure organic crystals, liquid organic solutions or plastic, polyvinyl, etc.

According to some embodiments, more than one scintillator can be coupled to each photodetector, or more than one photodetector can be coupled to each scintillator.

The photodetectors 26 are conventionally mounted on a supporting substrate 28, which can be in the form of a ceramic, a printed circuit board (PCB) or any other suitable supporting device that are well-known in the art for electrical coupling with the photon-counting electronics 20. Each photodetector 26 is in the form of an amplifying device such as an avalanche photodiode (APD) or an array of APDs. The amplifying photodetector devices are operated in a linear multiplication mode, where the output charge is proportional to the number of scintillation light photons measured by the photodetector 26 multiplied by the amplification gain of the device, or in Geiger mode where a single or a few incident photons trigger an avalanche breakdown resulting in a large signal whose amplitude is determined by the readout circuit.

According to another embodiment, the photodetectors 26 are in the form of an array of small avalanche photodiode cells known as silicon photomultiplier (SiPM) devices, solid state photomultiplier (SSPM) Geiger-mode avalanche photodiode (G-APD), or multicell avalanche diode (MAD), which are operated in a mode producing, in response to the radiation characterizing signals from the scintillator, corresponding electric signals that are coarsely proportional to the energy of the radiation.

In operation, the X-ray impinging in the crystal creates hundreds to thousands of scintillation light photons in the crystal lattice. The light emitted is then brought to the surface of the photodetector 26.

The use of fast scintillators avoids pulse pileup and detector dead time and eliminates image lag due to the charge migration time in semiconductor materials. The scintillator 24 can also be made to achieve nearly 100% detection efficiency in the diagnostic energy range. This last feature and the fact that the electronics are operated in photon counting mode, as will be explained hereinbelow in more detail, eliminates noise integration and makes the detector a quasi-ideal detector as defined by DQE (detective quantum efficiency) analysis, which is an important figure of merit in CT system performance analysis.

Even though the detector array 16 has been illustrated in FIG. 3 as being a multi-slice, it can also be a single slice. More generally, the geometry of the array may of course be different than illustrated in FIG. 3 and so is the number of pixel detectors 23 forming the array 16.

The photon-counting electronics 20 will now be described in more detail with references to FIG. 4. As will now become more apparent, the photon-counting electronics 20 are configured for measuring and recording the count rate of the individual pixel 23.

The photon-counting electronics 20 include a preamplifier 30 downstream from the photodetector 26, a discrete event circuitry 32 coupled to the preamplifier 30 downstream therefrom and a data processor 34 coupled to the discrete event circuitry 32 and located downstream therefrom.

The discrete event circuitry 32 and data processor 34 allows performing pulse shape analysis on the signal generated by the photodetectors 26 after pre-processing by the preamplifier 30. The analysis aims at discriminating individual X-ray photons based on analog or digital signal processing and discrimination. Since these signal processing and discrimination methods are believed to be well known in the art, they will not be described herein in more detail.

Of course, when the system 10 comprises an array of detectors 26 with corresponding scintillators 24, the photon-counting electronics 20 includes parallel electronic channels capable of simultaneously processing signals incoming from the array 16. Such channels can be made independent or not from one another.

Characteristics and functions of the photon-counting electronics 20 will become more apparent upon reading the following description of the operation thereof.

In operation, the signal generated by the photodetector 26 is first amplified and shaped by the low noise preamplifier 30, which can be a transimpedance (voltage sensitive), a transconductance (charge sensitive) preamplifier, or a simple operational amplifier as determined by the photodetector signal characteristics and which is well known in the art.

Figure 5:
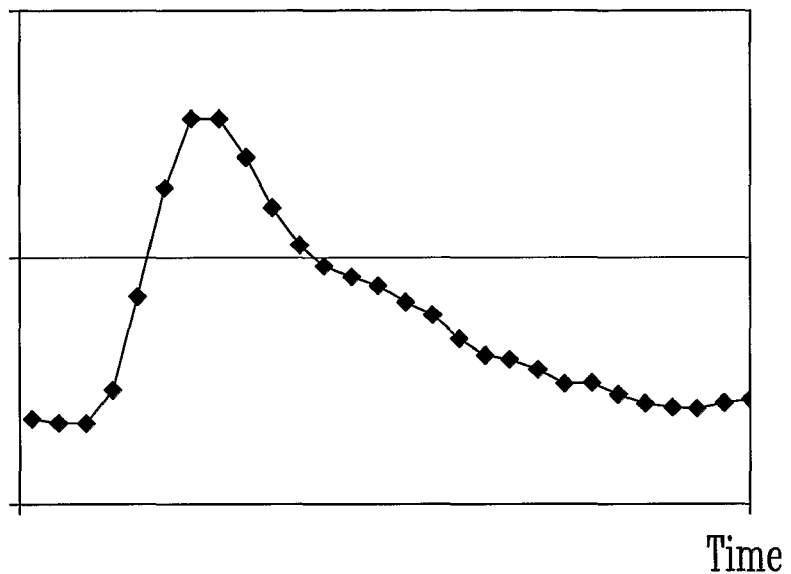
FIG. 5 is a graph of a typical signal obtained at the output of the preamplifier from the photon-counting electronics from FIG. 4.

FIG. 5 illustrates a typical signal obtained at the output of a low-noise charge sensitive preamplifier 30 by the photoelectric interaction of a 60 keV X-ray in a detector pixel 24. In this specific example, the signal was sampled at 45 mega-samples-per-second (MSPS) using the digital processing electronic system 20 described herein. The line represents the lower level discriminator for accepting events, wherein all events with amplitude larger than this threshold are accepted while others are ignored.

Several options are then available for further processing of the signal and registration of the detected event which are illustrated by the discrete event circuitry 32 and data processor 34 in FIG. 4. According to a relatively simple implementation of the photon-counting electronics 20, the discrete event circuitry 32 includes a simple discriminator threshold to trigger a counter whenever the photon signature signal issued by the detector pixel 23 exceeds the discriminator level. The counter is then read out and encoded with the detector address within the detector array and position at the end of each projection measurement by the data processor 34. The position is characterized by the position step of the rotating detector assembly 16 and X-ray source 14.

In a more elaborate implementation of the photon-counting electronics 20, the maximum of the signal is detected and then digitized by the discrete event circuitry 32, which includes an analog to digital converter (ADC) to determine the signal amplitude, which is proportional to the X-ray energy. The resulting digitized data are stored in histogram form to preserve the energy information and be transferred together with the encoded detector address and position at the end of each projection measurement by data processor 34. Alternatively, the digitized data can be transferred event-by-event, after being encoded with the detector address and position by data processor 34, to the controller 22 for storage in histogram- or list-mode format. According to yet another embodiment, the signal is directly digitized at the output of the preamplifier with a free-running ADC in the discrete event circuitry 32 and the digitized data samples are transferred to digital signal processors 34 for real-time analysis, as described hereinabove.

Figure 6:
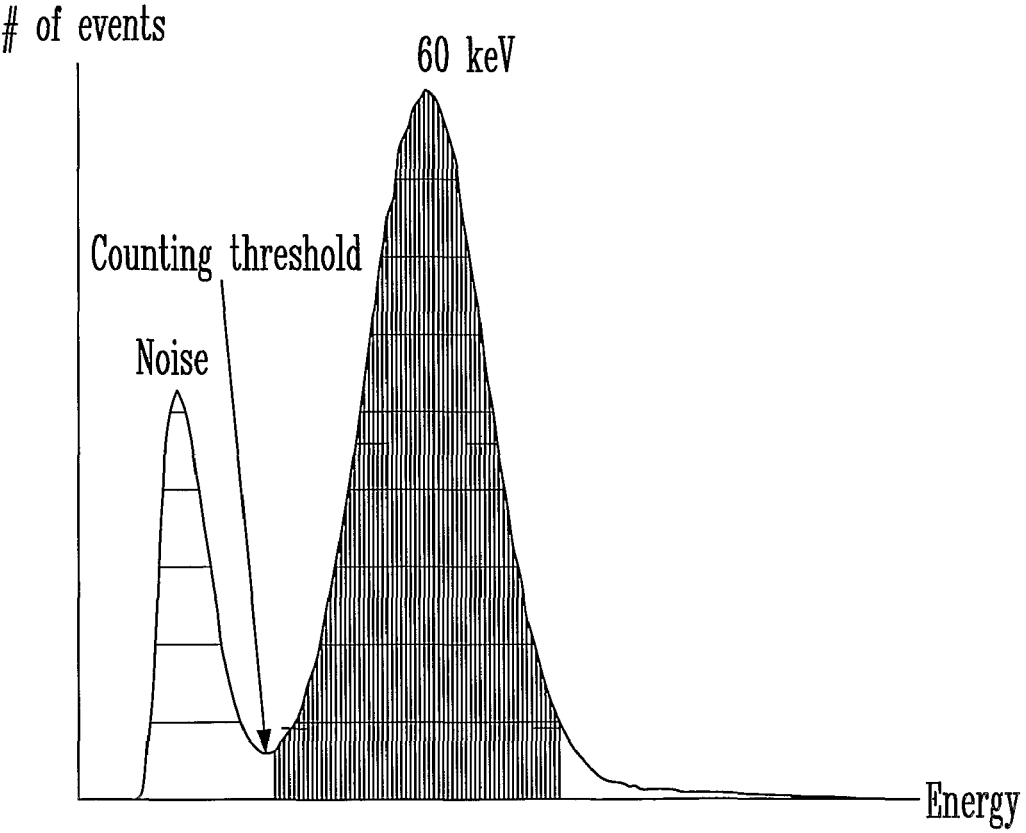
FIG. 6 is a graph of a typical energy spectrum of an X-ray radiation obtained with an APD-based detector, illustrating a lower level threshold for accepting events in a photon counting mode according to the present invention.

FIG. 6 illustrates an energy spectrum obtained with a detector as described herein and illustrated in FIG. 3. The spectrum was obtained with the described electronics 20. The spectrum shows the photoelectric peak of 60 keV photons resulting of the disintegration of $^{241}$Am. The peak can clearly be distinguished from the electronic noise. The lower discrimination threshold is shown as an example of how the valid events measured by the detector 16 can be selected. The energy spectrum shown was selected to illustrate the discrimination ability of the detection system for monochromatic radiation, but similar data can be obtained using an X-ray tube with a range of different X-ray energies.

In summary, a method 100 for low radiation computed tomography according to an illustrative embodiment of the present invention comprises the following steps, which are illustrated in FIG. 7:

102—receiving a subject on the subject-receiving area;

104—pivoting in unison both the low-energy radiation source and the detector assembly from a predetermined angular range;

106—directing a low-energy radiation source towards the subject at least at some angular position within said angular range, causing radiation to be transmitted through the subject towards the detector;

108—detecting and recording position and energy of individual transmitted photons; and

110—creating a CT image using the position and energy of the transmitted photons.

In step 106, the low-energy radiation source is operated either continuously or in a well known step-and-shoot mode where radiation are emitted only at some predetermined angular position within the angular range.

Although the present invention has been described hereinabove by way of preferred embodiments thereof, it can be modified without departing from the spirit and nature of the subject invention, as defined in the appended claims.

REFERENCES

1. R. N. Cahn, B. Cederström, M. Danielsson, A. Hall, M. Lundqvist, D. Nygren, Detective quantum efficiency dependence on X-ray energy weighting in mammography, *Medical Physics* 26(2), pp. 2680-2683, December 1999.
2. E. Beuville, R. Cahn, B. Cederstrom, M. Danielsson, A. Hall, B. Hasegawa, L. Luo, M. Lundqvist, D. Nygren, E. Oltman, J. Walton, High resolution X-ray imaging using a silicon strip detector, IEEE Transactions on Nuclear Science 45(6/2), 3059-3063, December 1998.
3. M. J. Paulus, H. Sari-Sarraf, S. S. Gleason, M. Bobrek, J. S. Hicks, D. K. Johnson, J. K. Behel, L. H. Thompson, W. C. Allen, A new X-ray computed tomography system for laboratory mouse imaging, IEEE Transactions on Nuclear Science 46(3/2), 558-564, June 1999.
4. J. U. Beusch, X-ray detector and method for measuring energy of individual X-ray photons for improved imaging of subjects using reduced dose, U.S. Pat. No. 5,665,969, Sep. 9, 1997.
5. R. Fontaine, F. Bélanger, J. Cadorette, J.-D. Leroux, J.-P. Martin, J.-B. Michaud, J.-F. Pratte, S. Robert, R. Lecomte, Architecture of a dual-modality, high-resolution, fully digital positron emission tomography/computed tomography (PET/CT) scanner for small animal imaging, IEEE Transactions on Nuclear Science 52(3/1), pp. 691-696, June 2005.

The invention claimed is:

1. A method for computed tomography (CT) comprising:
    providing a low energy radiation source oriented towards a subject-receiving area;
    providing a detector assembly positioned beyond said low-energy radiation source relative to said subject-receiving area; said low energy radiation source and said detector assembly being pivotable in unison about said subject-receiving area;
    receiving a subject on said subject-receiving area;
    pivoting in unison both said low-energy radiation source and said detector assembly from a predetermined angular range;
    directing said low-energy radiation source towards said subject at least at some angular position within said angular range, causing radiation to be transmitted through said subject towards said detector; said radiation transmitted through said subject towards said detector including transmitted photons;
    detecting and recording position and energy of individual of said transmitted photons; and
    creating a CT image from said position and energy of said transmitted photons.

2. A method as recited in claim 1, wherein said low energy radiation source is an X-ray source emitting an X-ray beam.

3. A method as recited in claim 2, wherein directing said low-energy radiation source towards said subject includes filtering said X-ray beam.

4. A method as recited in claim 2, wherein directing said low-energy radiation source towards said subject includes collimating said X-ray beam.

5. A method as recited in claim 1, wherein said some angular position within said angular range includes all angular position within said angular range.

6. A method as recited in claim 1, wherein said detector assembly includes a plurality of detector pixels for detecting low-energy photons; said detecting and recording position and energy of individual said transmitted photons yields a photon signature signal; detecting and recording position and energy of individual said transmitted photons includes triggering a counter when said photon signature signal exceeds a threshold.

7. A method as recited in claim 6, wherein each of said plurality of detector pixels is assigned an address and is characterized by a detector position; said detecting and recording position and energy of individual said transmitted photons further including encoding said detector address and position with said position of said individual of said transmitted photons and said counter.

8. A method as recited in claim 1, wherein said detector assembly includes a plurality of detector pixels for detecting low-energy photons; said detecting and recording position and energy of individual said transmitted photons yields a photon signature signal; detecting and recording position and energy of individual said transmitted photons includes detecting the maximum of a signal indicative of said photon signature.

9. A method as recited in claim 8, wherein each of said plurality of detector pixels is assigned an address and is characterized by a position; said detecting and recording position and energy of individual of said transmitted photons further including encoding said detector address and position with said position of said individual of said transmitted photons and said maximum of a signal indicative of said photon signature.

10. A system for computed tomography (CT) comprising:
    a subject-receiving area for receiving a subject;
    a low energy radiation source oriented towards said subject-receiving area;
    a photon-counting detector assembly positioned beyond said low-energy radiation source relative to said subject-receiving area; said low energy radiation source and said photon-counting detector assembly being pivotable in unison about said subject-receiving area; said photon-counting detector assembly including at least one detector pixel for detecting and recording position and energy of individual photons from said low energy radiation source transmitted from said subject;

photon-counting electronics coupled to each said photon-counting detector pixel for measuring and recording count-rate of said at least one detector pixel; and a signal processor coupled to said photon-counting electronics for creating CT image from said count-rate of said at least one detector pixel.

11. A system as recited in claim 10, wherein said detector assembly includes a plurality of detector pixels for detecting X-ray photons.

12. A system as recited in claim 11, wherein each said detector pixels includes at least one scintillator and a photodetector optically coupled to said at least one scintillator; each said photodetector being coupled to said photon-counting electronics.

13. A system as recited in claim 12, wherein said detector pixel includes a plurality of scintillators; at least one of said plurality of scintillators being responsive to said individual X-ray photons.

14. A system as recited in claim 13, wherein said at least one of said plurality of scintillators being responsive to said individual X-ray photons including a plurality of scintillators responsive to said individual X-ray photons; said photon-counting electronics being further configured to discriminate said plurality of scintillators responsive to said individual X-ray photons.

15. A system as recited in claim 14, wherein said photon-counting electronics are programmed with a pulse shape analysis method to discriminate said plurality of scintillators responsive to said individual X-ray photons.

16. A system as recited in claim 15, wherein said pulse shape analysis method includes at least one of digital identification and vector quantization methods.

17. A system as recited in claim 12, wherein said photodetector is in the form of an amplifying device.

18. A system as recited in claim 17, wherein said amplifying device is operable in one of a linear multiplication mode and a Geiger mode.

19. A system as recited in claim 12, wherein said photodetector is in the form of an avalanche photodiode (APD).

20. A system as recited in claim 19, wherein said avalanche photodiode is operated in a linear multiplication mode.

21. A system as recited in claim 19, where in said avalanche photodiode is operated in a Geiger mode.

22. A system as recited in claim 12, wherein said photodetector is in the form of a silicon photomultiplier device (SiPM), having an array of small avalanche photodiode (APD) cells.

23. A system as recited in claim 22, wherein said SiPM is operated in such a way that each said APD cells is operated in a Geiger mode, yielding an amplitude signal; a sum of amplitude signals from said APD cells providing a linear multiplication mode having an output signal proportional to a number of said APD cells being activated; said number of said APD cells being activated being coarsely proportional to a number of scintillation light photons generated in said at least one scintillator as a result of an interaction with an X-ray photon.

24. A system as recited in claim 12, wherein said scintillator is coated or wrapped with a high reflectivity material.

25. A system as recited in claim 10, wherein said scintillator is made of a material having a high photoelectric interaction probability for X-ray in the diagnostic energy range.

26. A system as recited in claim 10, wherein said scintillator is made of a fast light emitting crystal material capable of detecting individual X-ray photon.

27. A system as recited in claim 26, wherein said crystal material is a cerium activated orthosilicate crystal material.

28. A system as recited in claim 27, wherein said crystal material is selected from the group consisting of LSO, LGSO and LYSO.

29. A system as recited in claim 10, wherein said scintillator is made of an organic material.

30. A system as recited in claim 10, wherein said at least one detector pixel being further configured for yielding a photon signature signal; said photon-counting electronics including a discriminator coupled to each said photon-counting detector pixel; said discriminator being characterized by a threshold and a counter;

whereby, in operation, said counter is triggered when said photon signature signal exceeds said discriminator threshold.

31. A system as recited in claim 10, wherein said photon-counting electronics includes a preamplifier coupled to said at least one detector pixel for reading out an output of said at least one detector pixel.

32. A system as recited in claim 31, wherein said preamplifier is a transimpedance or a transconductance amplifier.

33. A system as recited in claim 10, wherein said photon-counting electronics include a discrete event circuitry.

34. A system as recited in claim 33, wherein said discrete event circuitry includes an analog processor.

35. A system as recited in claim 34, wherein said at least one detector pixel being further configured for yielding a photon signature signal; said analog processor being in the form of a discriminator coupled to each said photon-counting detector pixel; said discriminator being characterized by a threshold and a counter;

whereby, in operation, said counter is triggered when said photon signature signal exceeds said discriminator threshold.

36. A system as recited in claim 33, wherein said discrete event circuitry is a digital processor.

37. A system as recited in claim 36, wherein each said at least one detector pixel is assigned an address characterizing a position of said at least one detector pixel; said digital processor including a maximum detector and an analog to digital converter (ADC) to determine an amplitude of said photon signature signal;

whereby, in operation, said amplitude and said address being used by said signal processor for creating said CT image.

38. A system as recited in claim 33, wherein said discrete event circuitry is a digital processor, including a sampler.

39. A system as recited in claim 38, wherein each said at least one detector pixel is assigned an address characterizing a position of said at least one detector pixel; said sampler in said digital processor being a free-running analog-to-digital converter (ADC) for digitizing the signal for further on-line or off-line digital processing to determine an amplitude of said photon signature signal;

whereby, in operation, said amplitude and said address being used by said signal processor for creating said CT image.

40. A system as recited in claim 10, wherein said photon-counting detector assembly includes a plurality of detector pixels; said photon-counting electronics including parallel electronic channels for simultaneously processing signals incoming from said plurality of detector pixels.

41. A system as recited in claim 10, wherein said low energy radiation source is an X-ray source.

42. A system as recited in claim 41, wherein said X-ray source is selected from the group consisting of an X-ray tube, a rotating target, and a dual spot.

43. A system as recited in claim 41, wherein said X-ray tube is of the microfocus type.

44. A system as recited in claim 43, wherein said X-ray tube is characterized by a current; said current being set to allow discrimination and counting of individual photons impinging on each of said photon-counting detector pixels.

45. A system as recited in claim 43, wherein said current is set below a threshold intensity so as to not exceed the electronics maximum counting rate.

46. A system as recited in claim 10, wherein said low energy radiation source and said photon-counting detector assembly are mounted in an enclosure pivotally mounted about said subject-receiving area.

47. A system as recited in claim 46, wherein said enclosure is in the form of a cylinder positioned about said subject-receiving area.

48. A system as recited in claim 47, wherein said subject-receiving area includes a bed.

49. A system as recited in claim 48, wherein said enclosure defines a pivoting axis; said bed being movable along said pivoting axis.

50. A system as recited in claim 49, wherein the system is operable as an ultra-fast spiral CT scanner.

51. A system as recited in claim 10, further comprising a filter mounted to said radiation source so as to be operatively coupled thereto.

52. A system as recited in claim 10, further comprising a controller coupled to said photon-counting detector assembly and electronics for controlling the acquisition parameters thereof.

53. A system as recited in claim 52, wherein said controller being for further processing said count-rate of said at least one detector pixel and for forming a complete projection data set therewith.

* * * * *